Figure 1:
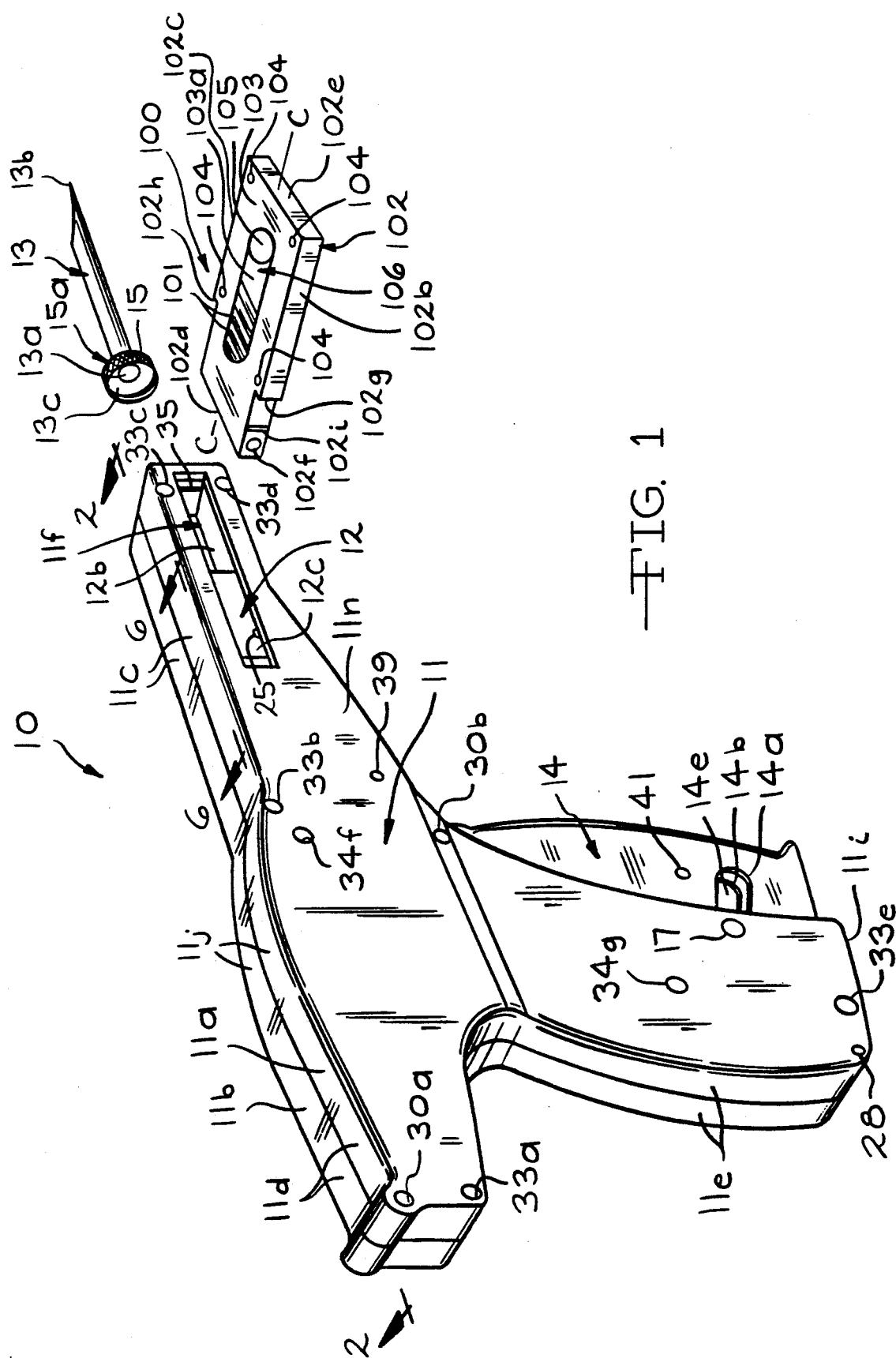

United States Patent [19]
Stewart

[11] Patent Number: 5,106,370
[45] Date of Patent: Apr. 21, 1992

[54] PELLET CARRIER FED PELLET IMPLANTER APPARATUS

[75] Inventor: R. Glen Stewart, Lake Villa, Ill.

[73] Assignee: Ideal Instruments, Inc., Chicago, Ill.

[21] Appl. No.: 719,391

[22] Filed: Jun. 24, 1991

Related U.S. Application Data

[63] Continuation-in-part of Ser. No. 644,531, Jan. 23, 1991.

[51] Int. Cl.$^5$ .................................... A61M 31/00
[52] U.S. Cl. ...................................... 604/61; 604/62; 604/64; 604/135
[58] Field of Search ....................... 604/60-64, 604/48, 59, 189, 137, 134, 135, 130, 95; 206/532, 534.1, 628, 537; 606/116, 117

[56] References Cited

U.S. PATENT DOCUMENTS

| | | |
|---|---|---|
| 3,669,104 | 6/1972 | Wyatt et al. |
| 3,774,607 | 11/1973 | Schmitz |
| 4,004,565 | 1/1977 | Fischer et al. |
| 4,077,406 | 3/1978 | Sandhage et al. |
| 4,403,610 | 9/1983 | Lodge et al. |
| 4,447,223 | 5/1984 | Kaye et al. |
| 4,474,572 | 10/1984 | McNaughton ................ 604/61 |
| 4,531,938 | 7/1985 | Kaye et al. |
| 4,576,591 | 3/1986 | Kaye et al. |
| 4,687,465 | 8/1987 | Prindle et al. |

FOREIGN PATENT DOCUMENTS 1583816  2/1981  United Kingdom .

Primary Examiner—Robert A. Hafer
Assistant Examiner—David J. Kenealy
Attorney, Agent, or Firm—Ian C. McLeod

[57] ABSTRACT

An improved automatic pellet carrier (100) fed pellet implanting gun apparatus (10) is described. The carrier is mounted in an opening (12b) through a front side (12c) of a retractable head (12) which is linearly moveable in a nose end (11c) of a handle assembly (11) along a longitudinal axis a—a. The carrier relies upon an internal spring (107) to automatically register a pellet (101) in a bore (12a) in the retractable head so that by actuating a trigger (14), a drive rod (23) which travels linearly along the axis a—a and through the bore in the retractable head and through the carrier, can move the pellet into the barrel (13a) of a needle (13) that has been inserted into an animal or the like. After the pellet enters the needle, the needle, the retractable head and the carrier are mechanically retracted into the gun with the carrier retracting along a slot (11f) in the nose so that the pellet is deposited in the animal, unobstructed by the needle. Releasing the trigger causes the retractable head, the needle and the carrier to return to their rest positions in the nose of the gun and the drive rod to move out of the bore in the retractable head and into the handle assembly so that the internal spring in the carrier can automatically register the next pellet in the carrier into the bore in the retractable head of the gun apparatus.

10 Claims, 5 Drawing Sheets

PELLET CARRIER FED PELLET IMPLANTER APPARATUS

CROSS-REFERENCE TO RELATED APPLICATION

This application is a continuation-in-part of U.S. application Ser. No. 07/644,531 filed Jan. 23, 1991 (Ideal 4.1-9) still pending.

BACKGROUND OF THE INVENTION (1) Field of the Invention

The present invention relates to an improved automatic pellet carrier fed pellet implanting apparatus particularly adapted for implanting medicament pellets in animals and the like. In particular, the present invention relates to an automatic gun apparatus for implanting medicament pellets which uses a pellet carrier for advancing pellets into an opening in the carrier. The carrier is preferably mounted in a side opening of a linearly moveable head assembly which is mounted in a nose section of the gun apparatus. A receiving slot is provided in a side wall of the nose section so that when the gun apparatus is actuated to implant a pellet, the carrier and the head assembly move in the gun apparatus, along a longitudinal axis with the carrier moving in the receiving slot towards the rear of the gun and away from the animal. The head assembly also mounts a hypodermic needle having a barrel for injecting the pellet into the animal. At the same time that the head assembly, the carrier and the needle move away from the animal, a pellet is advanced into the animal by a drive rod traveling along the longitudinal axis and through a bore in the head assembly, the opening in the carrier and through the barrel of the needle, with the pellet being deposited in the animal unobstructed by the needle. Releasing the trigger causes a first return spring means to return the head assembly, the needle and the carrier to the front of the gun apparatus while a second return spring retracts the drive rod along the axis to the back of the gun apparatus. Once the drive rod has left the bore in the head assembly, the pellets in the carrier are advanced along a second, perpendicular axis by a spring actuated plate in the carrier, to register the next pellet in the carrier in the opening through the carrier along the longitudinal axis.

(2) Prior Art

The prior art has described various types of hand held pellet implanting gun apparatus. These gun apparatus use essentially two types of carriers for medicament pellets for implanting in animals and the like. The first type uses a rigid rectangular cross-sectioned pellet carrier that is mounted at the front of the gun apparatus adjacent to a hypodermic needle. A trigger actuated drive rod in the gun apparatus travels through an indexed pellet chamber along a longitudinal axis and moves a pellet into the needle for implanting. After the pellet has been implanted and the trigger has been released, a mechanical mechanism advances the carrier along a second axis that is perpendicular to the longitudinal axis for registering the next pellet chamber in the carrier along the longitudinal axis. The rectangular carrier type of gun apparatus has numerous mechanical components and requires considerable precision in order for the gun apparatus to function. Illustrative of the rectangular pellet carriers are U.S. Pat. No. 4,004,565 to Fischer et al; U.S. Pat. No. 4,077,406 to Sandhage et al; U.S. Pat. No. 4,403,610 to Lodge et al; U.S. Pat. No. 4,447,223 to Kaye et al; and U.S. Pat. No. 4,687,465 to Prindle et al. British Patent No. 1,583,816 to Turley is also illustrative of the rectangular type of pellet carriers.

The second type of gun apparatus uses a cylindrical carrier that is mounted in a housing at the front of the gun apparatus. In the cylindrical type carriers, after a trigger actuated drive rod travels through an indexed pellet chamber and moves a pellet along a longitudinal axis and into a hypodermic needle for implanting, a mechanical mechanism rotates the carrier in a plane perpendicular to the longitudinal axis to register the next pellet chamber along the axis. The cylindrical carriers are similar to the rectangular carriers in that neither type of carrier travels linearly along the longitudinal axis when the trigger is actuated to implant a pellet into an animal and the like. The cylindrical carrier type of gun apparatus has numerous mechanical components and requires considerable precision in order for the gun apparatus to function. Illustrative of the cylindrical carriers are U.S. Pat. Nos. 3,669,104 to Wyatt et al; 3,774,607 to Schmitz; 4,531,938 to Kaye et al; and 4,576,591 to Kaye et al.

OBJECTS

It is therefore an object of the present invention to provide a pellet implanting gun apparatus with a pellet carrier for implanting in animals and the like, wherein the carrier moves linearly along a longitudinal axis corresponding to the axis the drive rod travels as it moves a pellet out of a chamber in the carrier and into a hypodermic needle that has been inserted into the animal. Further, it is an object of the present invention to provide a pellet implanting gun apparatus with a medicament pellet carrier that is easily mounted in a receiving slot through the head assembly that also supports the hypodermic needle. Further, it is an object of the present invention to provide a pellet implanting gun apparatus that provides for mounting a medicament pellet carrier that has an internal advancing mechanism for registering the pellets along an axis traveled by a drive rod for implanting the pellets into an animal and the like. Still further, it is an object of the present invention to provide a pellet carrier that is easy to fill with medicament pellets, that is easy to mount in a receiving slot in the gun apparatus and which is simply constructed and inexpensive to manufacture. These and other objects will become increasingly apparent by reference to the following drawings and the descriptions.

IN THE DRAWINGS

FIG. 1 is a right side isometric view of the pellet implanting gun apparatus 10 particularly illustrating a handle 11, a head assembly 12 which mounts a carrier 100 with pellets 101, a needle 13 and a trigger 14.

Figure 2:
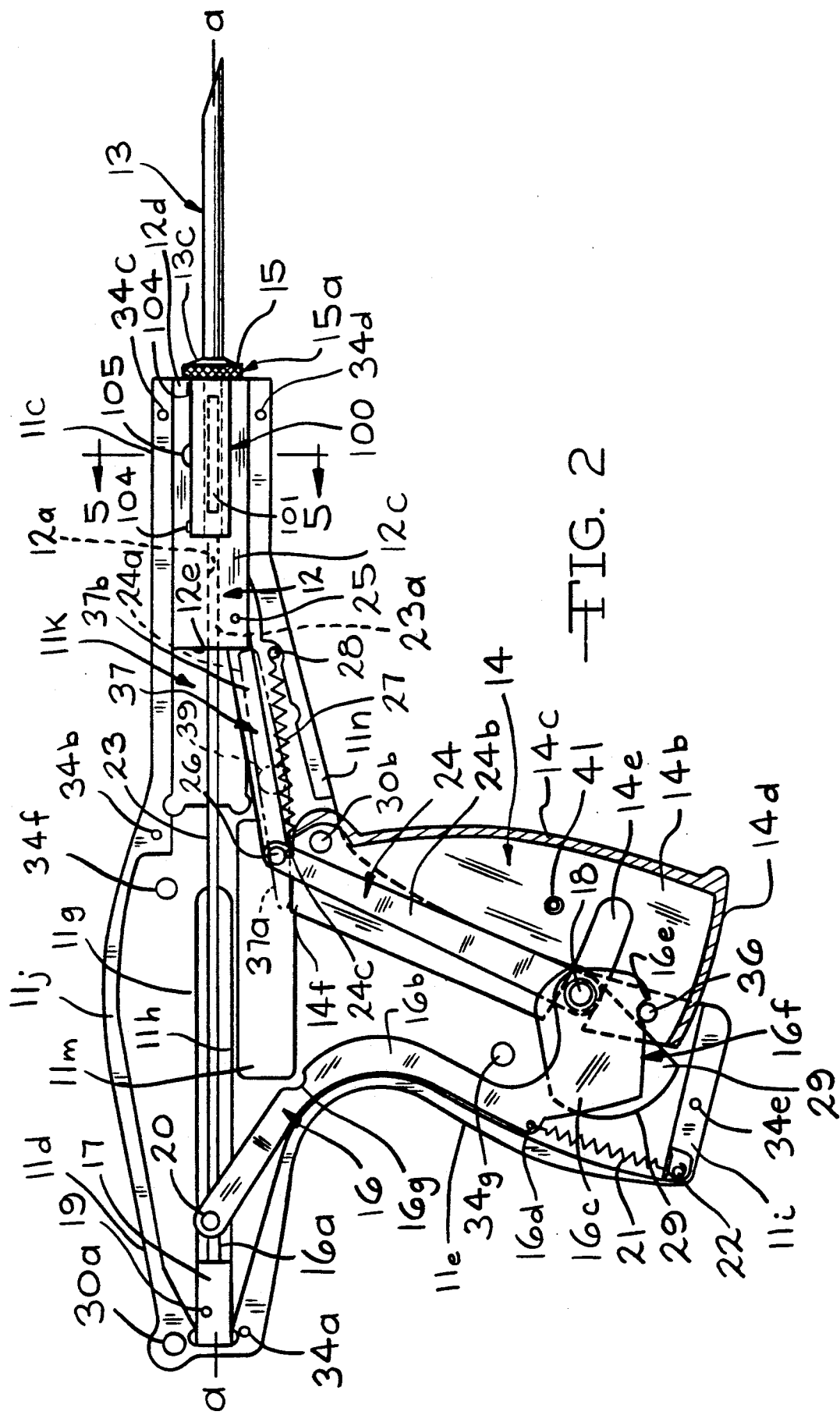

FIG. 2 is a right side, front cross-sectional view along line 2—2 of FIG. 1 showing the trigger 14 and actuated linkages 16 and 24 which connect to the head assembly 12 and a drive rod 21 in the rest position.

Figure 3:
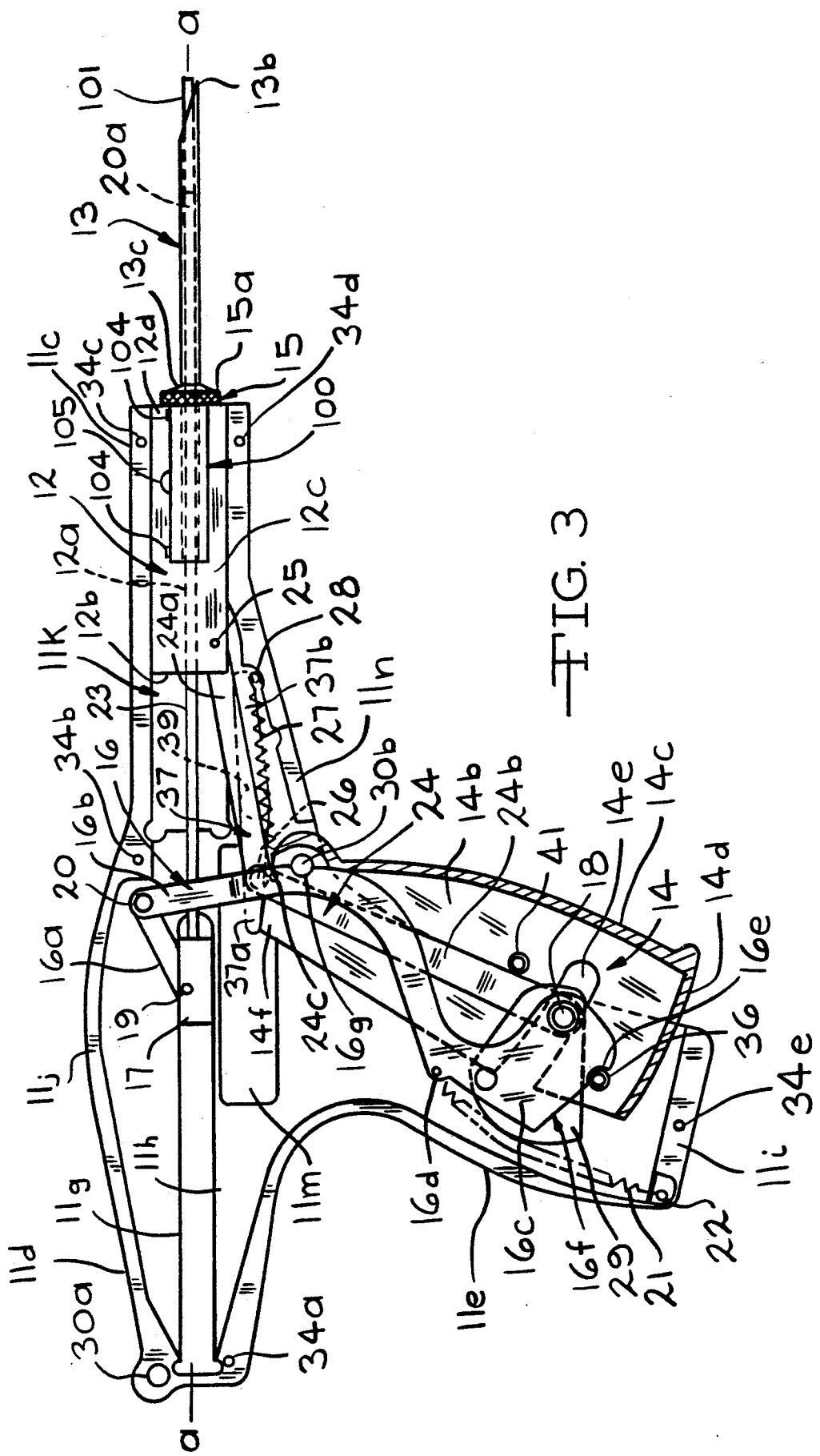

FIG. 3 is a right side, front view of the pellet implanting gun apparatus 10 showing the trigger 14 partially depressed wherein the pivotable linkage 16 has actuated the drive rod 23 and pellet 101 through the head assembly 12 and into the barrel 13.

Figure 4:
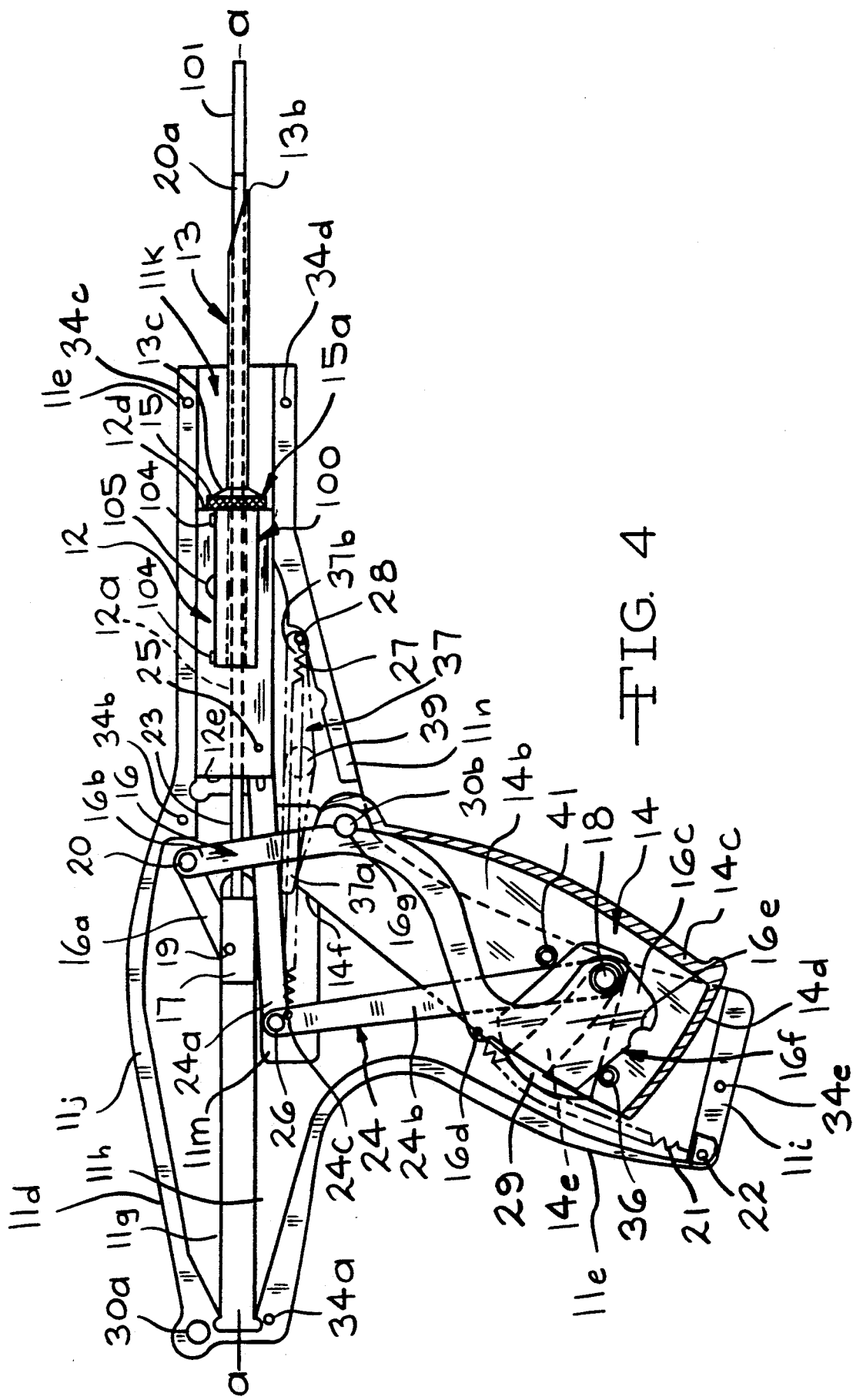

FIG. 4 is a right side, front view of the pellet implanting gun apparatus 10 showing the trigger 14 fully depressed wherein the pivotable linkage 24 has actuated the head assembly 12 to pull the needle 13 into the handle 11.

Figure 5:
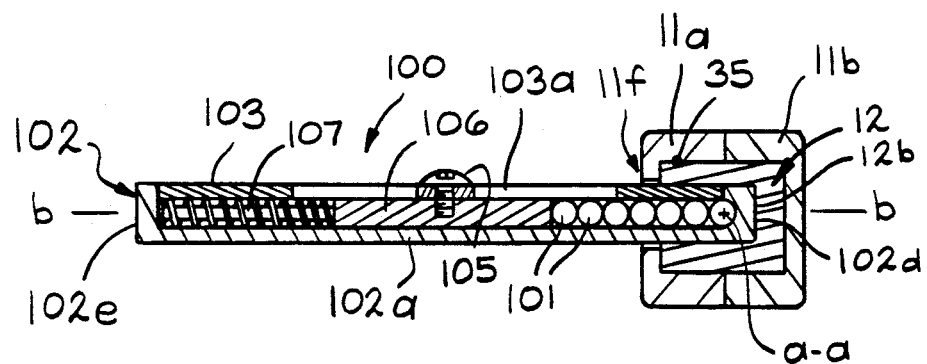

FIG. 5 is a cross-sectional view along line 5—5 of FIG. 2 showing the carrier 100 with pellets 101 inserted into the head assembly 12.

Figure 5A:
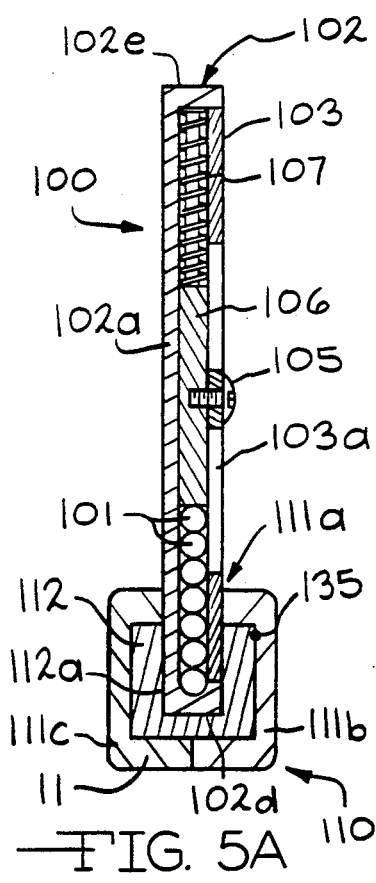

FIG. 5A is a cross-sectional view showing the carrier 100 with pellets 101 vertically mounted in a gun apparatus 110 comprised of a handle assembly 111 that is slideably mounted in a head assembly 112.

Figure 6:
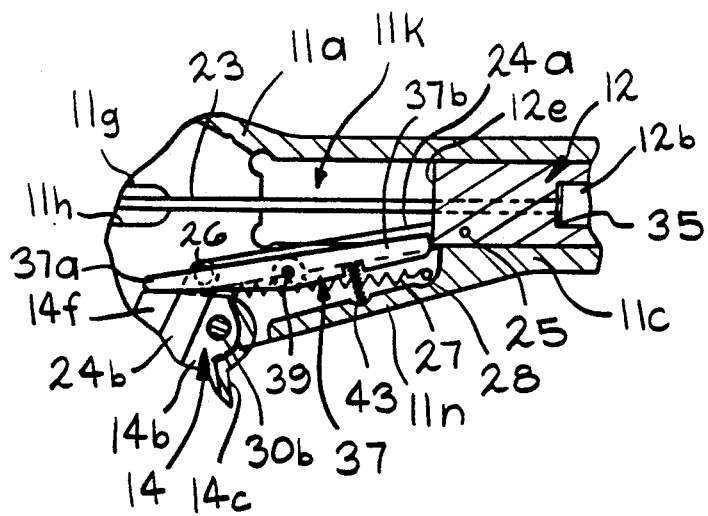

FIG. 6 is a cross-sectional view along line 6—6 of FIG. 1 showing a locking lever 37 holding the head assembly 12 in the handle 11.

GENERAL DESCRIPTION

The present invention relates to a hand held gun apparatus for implanting a pellet into an animal which comprises: a hollow needle having a barrel for implanting the pellet into the animal along a longitudinal axis of the needle; a head means being linearly moveable in the gun apparatus along the longitudinal axis, the head means supporting the needle with a first opening along the longitudinal axis and through the head means and into the barrel of the needle, and the head means having a second opening; a carrier means detachably mounted in the second opening in the head means along a second axis, perpendicular to the longitudinal axis, wherein the carrier means is linearly moveable with the head means along the longitudinal axis in a slot in the gun apparatus and provides for a plurality of pellets and wherein the carrier means holds a first pellet along the longitudinal axis and the first opening in the head means so that the first pellet can pass through an opening in the carrier means and the barrel of the needle; a pistol grip means supporting the head means; a drive rod mounted in the pistol grip means and linearly moveable through the first opening in the head means and into the barrel of the needle along the longitudinal axis from the pistol grip means; a trigger means mounted on the pistol grip means and actuatable by the finger; an actuating means mounted in the pistol grip means for moving the drive rod and for moving the head means upon actuating the trigger means; and a return means for moving the drive rod back into the pistol grip means and for moving the head means supporting the needle and the carrier means back into a rest position along the longitudinal axis and along the slot in the gun apparatus after the trigger means has been released.

Furthermore, the present invention relates to a hand held gun apparatus for implanting a pellet into an animal which comprises: a hollow needle having a barrel for implanting the pellet into the animal along a longitudinal axis of the needle; a head means mounted in a nose of the gun apparatus and being linearly moveable in the gun apparatus along the longitudinal axis, the head means supporting the needle with a first opening along the longitudinal axis and through the head means and into the barrel of the needle, and the head means having a second opening; a carrier means detachably mounted in the second opening of the head means along a second axis perpendicular to the longitudinal axis, wherein the carrier means is linearly moveable with the head means along the longitudinal axis in a slot in the nose of the gun apparatus and provides for a plurality of pellets and wherein the carrier means holds a first pellet in an opening through the carrier means along the longitudinal axis and the first opening in the head means so that the first pellet can pass through an opening in the carrier means and the barrel of the needle; a pistol grip means supporting the head means; a drive rod mounted in the pistol grip means and linearly moveable through the first opening in the head means and into the barrel of the needle along the longitudinal axis from the pistol grip means; a first actuating means mounted in the pistol grip means for moving the drive rod; a second actuating means mounted in the pistol grip means for moving the head means; a trigger means mounted on the pistol grip means and actuatable by the fingers to move the first actuating means and the second actuating means, wherein the first actuating means moves the drive rod into the first opening in the head means and into the opening through the carrier means where the drive rod engages the first pellet to move the first pellet through the opening in the carrier means, through the first opening in the head means and into the barrel of the needle and wherein the second actuating means moves the head means, supporting the needle and the carrier means, into the pistol grip means with the carrier means moving in the slot in the nose of the gun apparatus after the drive rod and the first pellet have moved into the barrel of the needle and wherein the trigger is then released; a first return means which moves the drive rod back into the pistol grip means after the trigger means has been released; and a second return means which moves the head means supporting the needle and the carrier means back into the nose of the gun apparatus along the longitudinal axis and along the slot in the nose of the gun apparatus after the trigger means has been released, wherein the advancing means of the carrier means registers a second pellet along the longitudinal axis in the head means after the first return means moves the drive rod out of the first opening in the head means and out of the opening in the carrier means and back into the pistol grip means and after the second return means moves the head means which supports the needle and the carrier means back into the nose of the gun apparatus.

In particular, the present invention relates to a hand held gun apparatus for implanting a pellet into an animal which comprises: a hollow needle having a barrel for implanting the pellet into the animal along a longitudinal axis of the needle; a head means mounted in a nose of the gun apparatus and being linearly moveable in the gun apparatus along the longitudinal axis, the head means supporting the needle at a first end and having a second end opposite the first end traversed by a first opening along the longitudinal axis and through the head means and into the barrel of the needle, and the head means having a second opening; a carrier means detachably mounted in the second opening of the head means along a second axis, perpendicular to the longitudinal axis, wherein the carrier means is linearly moveable with the head means along the longitudinal axis in a slot in the nose of the gun apparatus and provides for a plurality of pellets and wherein the carrier means holds a first pellet in an opening through the carrier means, and along the longitudinal axis and the first opening through the head means so that the first pellet can pass through the barrel of the needle; a pistol grip means supporting the head means; a drive rod mounted on the pistol grip means and linearly moveable along the longitudinal axis and through the first opening between the first and second ends of the head means and into the barrel of the needle; a first actuating means mounted inside of the pistol grip means for moving the drive rod; a second actuating means mounted in the pistol grip means for moving the head means; a trigger means mounted on the pistol grip means and actuatable by the fingers to move the first actuating means and the second actuating means, wherein when the trigger means is actuated, the trigger means engages a first linkage means forming the first actuating means which moves the drive rod into the first opening in the head means and into the opening through the carrier means where the drive rod engages the first pellet and moves the first pellet through the opening in the carrier means, through the first opening in the head means and into the barrel of the needle and wherein when the trigger means is actuated, the trigger means engages a second linkage means forming the second actuating means which moves the head means supporting the needle and the carrier means into the pistol grip means with the carrier means moving in the slot in the nose of the gun apparatus, after the drive rod and the first pellet have moved into the barrel of the needle, and wherein the trigger is then released; a first spring means for moving the drive rod back into the pistol grip means after the trigger means has been released; and a second spring means for moving the head means, supporting the needle and the carrier means, back into the nose of the gun apparatus along the longitudinal axis and along the slot in the nose of the gun apparatus after the trigger means has been released wherein a second pellet in the carrier means is registered along the longitudinal axis in the head means after the first spring means moves the drive rod out of the first opening in the head means and out of the opening in the carrier means and back into the pistol grip means and after the second spring means moves the head means which supports the needle back into the nose of the gun apparatus.

Finally, the present invention relates to a carrier device for pellets to be injected by means of a hand held gun apparatus which comprises: an elongated bar means having opposed top and bottom ends, opposed front and rear sides and first and second lateral sides between the top and bottom ends wherein there are spaced apart first and second openings in the first and second lateral sides adjacent to the top end, the bar means adapted to be mounted in a head means of the gun apparatus and linearly moveable along the longitudinal axis in a slot in the gun apparatus so that a drive rod can enter the first opening on the first lateral side and move a first pellet out of the second opening in the second lateral side along the longitudinal axis and into a barrel in a needle for implanting the pellet; and a spring means for urging a plate means mounted between the first and second sides of the bar means, from the bottom end to the top end of the bar means so that the plate means advances the pellets along a second axis, perpendicular to the longitudinal axis, for registering a second pellet between the first and second openings in the first and second lateral sides after the return means for the drive rod has moved the drive rod out of the first and second openings in the first and second lateral sides of the bar means.

Thus, the present invention in one embodiment relies upon an internal advancing means inside the pellet carrier to automatically register a pellet in the gun apparatus along the longitudinal axis so that the drive rod which travels linearly along the longitudinal axis can move the pellet into the needle that has been inserted into an animal. After the pellet has been moved into the needle, the needle is mechanically retracted into the gun apparatus along the longitudinal axis so that the pellet is deposited in the animal unobstructed by the needle.

Another possible embodiment of the present invention consists of a pellet carrier that is in a ratchet engagement with a pawl for advancing the carrier through the second opening, along the second axis of the head means. That way, after the gun apparatus has been actuated to implant a first medicament pellet, the trigger is released and the pawl engages the ratchet teeth on the pellet carrier, causing the carrier to advance along the second opening through the head means to register a second medicament pellet along the first opening through the head means. Such a mechanism is used in revolvers, for instance.

Still another possible embodiment of the present invention consists of a manually operated lever mounted on the moveable head means that is actuated to advance the pellet carrier along the second opening through the head means, after a first medicament pellet has moved from a first pellet chamber and been implanted into an animal. Actuating the lever causes a cam member to engage a first advancing means corresponding to the first pellet chamber which advances the carrier along the second axis to thereby register a second pellet chamber along the first opening through the head means. The lever is then released to move back into a rest position with the cam member moving back over a second advancing means corresponding to the second chamber. A second pellet in the second chamber is now aligned along the first opening through the head means for implanting into an animal. Such advancing means are known where the carrier is in a fixed position

SPECIFIC DESCRIPTION

FIGS. 1 to 6 show a pellet implanting gun apparatus 10 of the present invention. The preferred form of the gun apparatus 10 includes a handle assembly 11, a head assembly 12 supporting a needle 13 and a trigger 14. The handle assembly 11 includes a right half 11a and a left half 11b (FIG. 1) which are mirror images of each other. The halves 11a and 11b have a nose end 11c, a butt end 11d and a grip portion 11e which receives the trigger 14 when the trigger 14 is actuated. A side slot 11f through the right half 11a of the handle assembly 11 in the nose 11c provides for linear movement of a carrier 100 with pellets 101.

The head assembly 12 has a rectangular cross-section along a plane perpendicular to the axis a—a and provides for an opening or bore 12a (FIG. 3). An opening 12b through the front side 12c of the head assembly 12 is in communication with the bore 12a for positioning the carrier 100 with pellets 101 along the axis a—a (FIG. 5).

The needle 13 has a barrel 13a with an angular taper forming into a pointed tip 13b at one end and a flanged section 13c at the other end. A nut 15 is mounted on the flanged section 13c and secures the needle 13 to the distal end 12d of the head assembly 12 adjacent to the opening 12b. The nut 15 has a gripping outer surface 15a to help remove the needle 13 from the head assembly 12 for changing and cleaning. The trigger 14 is formed of spaced apart plates 14a and 14b (FIG. 1) which are mirror images of each other and which are connected together by a front plate 14c and a bottom plate 14d.

As shown in FIG. 2, when the gun apparatus 10 is in the rest position, a first pivotable linkage 16 extends from a rod holder 17 to a shuttle linkage pivot pin 18 mounted between the two halves 11a and 11b of the handle assembly 11 adjacent to an arcuate slot 14e in the trigger 14. Pivotable linkage 16 is comprised of linkage members 16a and 16b. Linkage member 16a is secured to the rod holder 17 through a securing slot (not shown) offset in front of the axis a—a (FIG. 5) by a roll pin 19 and extends to a linkage pin 20. The linkage pin 20 pivotably secures the linkage member 16a to the linkage member 16b which extends to the shuttle linkage pivot pin 18. The linkage member 16b has a serpentine shape with an enlarged section 16c at its lower end. A return spring 21 is mounted between an opening 16d adjacent to the enlarged section 16c and a securing post 22 mounted in the bottom 11i of the handle assembly 11 to hold the linkage members 16a and 16b in the rest position. The return spring 21 serves to return the first pivotable linkage 16 and a drive rod 23 mounting the rod holder 17 to their respective rest positions after the gun apparatus 10 has been activated to release a pellet 101.

A second pivotable linkage 24, comprised of linkage members 24a and 24b, extends from the proximal end 12e of the head assembly 12 to the shuttle link pivot pin 18. Linkage member 24a is secured to the proximal end 12e of the head assembly 12, offset behind the axis a—a (FIG. 5) in a securing slot (not shown) by a roll pin 25 and extends to a linkage pin 26. Linkage pin 26 pivotably secures the linkage member 24a to the linkage member 24b which extends to the shuttle' linkage pivot pin 18.

When the trigger 14 is in the rest position (FIG. 2), the drive rod 23 is positioned between the bore 12a in the head assembly 12 and the butt end 11d of the handle assembly 11. The drive rod 23 is linearly slideable along the axis a—a through the bore 12a and into the barrel 13a of needle 13. The drive rod 23 is moved along parallel side rails 11g and 11h on each half 11a and 11b of the handle assembly 11 by the rod holder 17 which slides between the rails 11g and 11h. A return spring 27 is mounted between an opening 24c in linkage member 24b adjacent to linkage pin 26 and a securing post 28 adjacent to the proximal end 12e of the head assembly 12 when the head assembly 12 is at rest. The return spring 27 serves to return the second pivotable linkage 24 and the head assembly 12 to their respective rest positions after the gun apparatus 10 has been fired.

A rounded back rest member 29 preferably made of teflon, is provided on shuttle linkage pivot pin 18 between linkage member 16b of the first pivotable linkage 16 and linkage member 24b of the second pivotable linkage 24. Rest member 29 serves both to reduce the wear on return spring 21 against the enlarged section 16c of pivotable linkage 16 and to reduce the sliding friction between the enlarged section 16c and linkage member 24b of the second pivotable linkage 24.

The right half 11a and the left half 11b of the handle assembly 11 are assembled together by lining up guide pin 30a, hinge pin 30b and shuttle linkage pivot pin 18. The two halves 11a and 11b are then secured together with set screws 33a, 33b, 33c, 33d and 33e (FIG. 1) through openings 34a, 34b, 34c, 34d and 34e (FIG. 2 to 4). Openings 34f and 34g act as safety mechanisms to prevent the gun apparatus 10 from firing when a guide pin (not shown) is inserted into the openings 34f and 34g.

A carrier 100 with a plurality of pellets 101 is horizontally mounted through the side slot 11f in the right half 11a of the handle assembly 11 and into the opening 12b in the front side 12c of the head assembly 12. The carrier 100 has a rectangular cross-section along the axis b—b and comprises a base plate 102 having a bottom wall 102a (FIG. 5) with spaced apart sidewalls 102b and 102c. The sidewalls 102b and 102c each provide for an opening 102f (only opening 102f through sidewall 102b shown in FIG. 1) adjacent to the end wall 102d that allows the user to fill the carrier 100 with pellets 101 and which also allows the pellets 101 to be ejected from the carrier 100 when the gun apparatus 10 is actuated. The sidewalls 102b and 102c have stepped portions 102g and 102h, respectively, spaced from the opening 102f. The side portions 102g and 102h abut against the front side 12c of the head assembly 12 when the carrier 100 is inserted through the side slot 11f and into the front side 12c of the head assembly 12. A top plate 103 is secured to the sidewalls 102b and 102c of the bottom plate 102 by mounting screws 104. The top plate 103 has a slot 103a that provides for movement of a screw 105 threadably mounted in a plate 106 biased by a spring 107 (FIG. 5). The carrier 100 is held in place in the opening 12b in the front side 12c of the head assembly 12 by a securing wire 35 (FIGS. 1, 5 and 6) that snappingly mates with a groove 102i (FIG. 1) in the sidewalls 102b and 102c (only 102b shown) of the carrier 100.

The orientation of the carrier around the axis a—a of the gun apparatus 10 is not critical as long as the pellets are fed into the gun apparatus 10 along an axis perpendicular to the axis a—a. As shown in FIG. 5A, the carrier 100 can be vertically mounted in a slot 111a formed in a right half 111b and a left half 111c of a handle assembly 111. The carrier 100 is mounted by a securing wire 135 similar to securing wire 35 that snappingly mates with the carrier 100. The handle assembly 111 is slideably mounted in an opening 112a in a head assembly 112 of a gun apparatus 110. In all other respects, the gun apparatus 110 is similar to the gun apparatus 10.

To load the carrier 100, the user slides the screw 105 towards the end wall 102e which compresses the spring 107. Pellets 101 are then inserted through the opening 102f in either sidewall 102b or 102c until the carrier 100 is full of pellets (partially shown in FIG. 5). As the pellets are ejected from the gun apparatus 10, the spring 107 advances the plate 106 and the row of pellets 101 so that the next pellet 101 is positioned along the axis a—a in the opening 102f of the carrier 100 in line with the bore 12a through the head assembly 12 and drive rod 23 for firing into an animal.

In operation, the pellets 101 are implanted subcutaneously into domestic animals such as cattle, sheep, horses and pigs. The pellets 101 are usually inserted into the animal's ear because an animal's ear has good blood circulation which allows the pellets 101 to effectively dissolve. Because an animal's ear is not consumed by humans, there is also little risk of a human ingesting a partially dissolved pellet 101.

To implant a pellet 101 into an animal, the needle 13 is first inserted into the animal's ear to the desired depth. The trigger 14 is then actuated by squeezing with the fingers. As shown in FIGS. 2 and 4, as the arcuate opening 14e in the trigger 14 moves over the shuttle linkage pivot pin 18, a lever roll pin 36, provided between the spaced apart plates 14a and 14b of the trigger 14 adjacent to the bottom plate 14d, rotates in a semicircular notch 16e in the enlarged section 16c of linkage member 16b before moving over a level surface 16f of the enlarged section 16d. When the force of the fingers squeezing on the trigger 14 is transferred to the linkage member 16b, the enlarged section 16c of linkage member 16b pivots on the shuttle link pivot pin 18, causing linkage member 16b to move towards the nose end 11c of the handle assembly 11. As the linkage member 16b moves forward, the linkage member 16a of the pivotable linkage 16 moves forward as well, stretching the return spring 21 and pulling the rod holder 17 and drive rod 23 forward through the head assembly 12 and into the needle 13. When this occurs, the linkage members 16a and 16b pivot on linkage pin 20 as the rod holder 17 travels substantially the entire distance of the parallel side rails 11g and 11h. The top 11j of the handle assembly 11 is arched to accommodate this movement.

As shown in FIG. 3, the arcuate movement of the linkage member 16b is complete when a semicircular notch 16g in linkage member 16b rests against the hinge pin 30b. At this point, when the lever roll pin 36 has stopped rotating in the semicircular notch 16g and is just beginning to travel over the level surface 16f of the enlarged section 16c, the rod holder 17 has traveled substantially the entire distance down the rails 11g and 11h of the handle assembly 11, the front end 23a of the drive rod 23 has engaged a pellet 101 in carrier 100 and pushed the pellet 101 out of the bore 12a in the head assembly 12 and through the barrel 13a in needle 13 to the pointed tip 13b at the end of the needle 13. At this time, when the forward movement of the drive rod 23 into the needle 13 is complete, the arcuate opening 14e in trigger 14 has traveled the majority of its arcuate extent over the shuttle linkage pivot pin 18. As shown in FIGS. 2 and 6, a head assembly lock 37 is mounted on the right half 11a of the handle assembly 11 adjacent to the upper end 14f of trigger 14 and the proximal end 12e of the head assembly 12. The head assembly lock 37 pivots on a fulcrum pin 39 and locks the head assembly 12 in place when the gun apparatus 10 is in the rest position. When the trigger 14 is actuated (FIG. 3), the upper end 14f of the trigger 14, opposite the hinge pin 30b, engages the left arm 37a of the head assembly lock 37, forcing the left arm 37a to pivot upward on fulcrum pin 39 towards the drive rod 23 so that the right arm 37b pivots downward towards the securing post 28, thereby unlocking the head assembly 12. The head assembly 12 is now free to travel backwards in a channel 11k formed in the nose end 11c of the handle assembly 11.

As shown in FIG. 3 when the drive rod 23 has substantially completed its travel through the needle 13, a lever roll pin 41 provided between the spaced apart plates 14a and 14b of the trigger 14 adjacent to the arcuate notch 14e, has just started to engage the linkage member 24b of the second pivotable linkage 24. Further movement of the trigger 14 into the handle assembly 11 causes lever roll pin 41 to force the linkage member 24b to pivot in an arcuate path around the shuttle linkage pivot pin 18. Movement of the linkage member 24b causes linkage member 24a to pivot on linkage pin 26 and move towards the butt end 11d of the handle assembly 11, stretching the return spring 27 and pulling the head assembly 12 and the needle 13 into the gun apparatus 10. The linkage pin 26 travels through a recess 11m provided in the left half 11b of the handle assembly 11 as the head assembly 12 travels substantially the entire length of the channel 11k. The head assembly 12 pulls the pointed tip 13b of needle 13 out of the animal's ear so that the animal tissue pierced by the needle 13, can close and envelope the pellet 101. The gun apparatus 10 is then pulled away from the animal and the trigger 14 is released. Releasing the trigger 14 lets the gun apparatus 10 return to its rest position as shown in FIG. 2. This occurs when the return spring 21 unstretches to return the first pivotable linkage 16 and the drive rod 23 with the drive rod holder 17 to their respective rest positions and when the return spring 27 unstretches to return the second pivotable linkage 24 and the head assembly 12 with the needle 13 and the carrier 100 to their respective rest positions. As the head assembly 12 returns to the nose end 11c of the handle assembly 11, a spring 43 (FIG. 6) provided between the right arm 37b of the head assembly lock 37 and the lower section 11n of the nose end 11c of the handle assembly 11, forces the right arm 37b upward so that it locks the head assembly 12 in the rest position.

Numerous variations will occur to those skilled in the art and it is intended that the present invention be limited only by the hereinafter appended claims.

I claim:

1. A hand held gun apparatus for implanting a pellet into an animal which comprises:
   (a) a hollow needle having a barrel for implanting the pellet into the animal along a longitudinal axis of the needle;
   (b) a head means being linearly moveable in the gun apparatus along the longitudinal axis, the head means supporting the needle with a first opening along the longitudinal axis and through the head means and into the barrel of the needle, and the head means having a second opening;
   (c) a carrier means detachably mounted in the second opening in the head means along a second axis, perpendicular to the longitudinal axis, wherein the carrier means is linearly moveable with the head means along the longitudinal axis in a slot in the gun apparatus and provides for a plurality of pellets and wherein the carrier means holds a first pellet along the longitudinal axis and the first opening in the head means so that the first pellet can pass through an opening in the carrier means and the barrel of the needle;
   (d) a pistol grip means supporting the head means;
   (e) a drive rod mounted in the pistol grip means and linearly moveable through the first opening in the head means and into the barrel of the needle along the longitudinal axis from the pistol grip means;
   (f) a trigger means mounted on the pistol grip means and actuatable by the finger;
   (g) an actuating means mounted in the pistol grip means for moving the drive rod and for moving the head means upon actuating the trigger means; and
   (h) a return means for moving the drive rod back into the pistol grip means and for moving the head means supporting the needle and the carrier means back into a rest position along the longitudinal axis and along the slot in the gun apparatus after the trigger means has been released.

2. The apparatus of claim 1 wherein the carrier means is comprised of a hollow bar means having spaced apart sides with an opening through the carrier means provided by a partially rounded wall between spaced apart openings in the sides of the carrier means.

3. A hand held gun apparatus for implanting a pellet into an animal which comprises:
   (a) a hollow needle having a barrel for implanting the pellet into the animal along a longitudinal axis of the needle;
   (b) a head means mounted in a nose of the gun apparatus and being linearly moveable in the gun apparatus along the longitudinal axis, the head means supporting the needle with a first opening along the longitudinal axis and through the head means and into the barrel of the needle, and the head means having a second opening;

(c) a carrier means detachably mounted in the second opening of the head means along a second axis perpendicular to the longitudinal axis, wherein the carrier means is linearly moveable with the head means along the longitudinal axis in a slot in the nose of the gun apparatus and provides for a plurality of pellets and wherein the carrier means holds a first pellet in an opening through the carrier means along the longitudinal axis and the first opening in the head means so that the first pellet can pass through an opening in the carrier means and the barrel of the needle;

(d) a pistol grip means supporting the head means;

(e) a drive rod mounted in the pistol grip means and linearly moveable through the first opening in the head means and into the barrel of the needle along the longitudinal axis from the pistol grip means;

(f) a first actuating means mounted in the pistol grip means for moving the drive rod;

(g) a second actuating means mounted in the pistol grip means for moving the head means;

(h) a trigger means mounted on the pistol grip means and actuatable by the fingers to move the first actuating means and the second actuating means, wherein the first actuating means moves the drive rod into the first opening in the head means and into the opening through the carrier means where the drive rod engages the first pellet to move the first pellet through the opening in the carrier means, through the first opening in the head means and into the barrel of the needle and wherein the second actuating means moves the head means, supporting the needle and the carrier means, into the pistol grip means with the carrier means moving in the slot in the nose of the gun apparatus after the drive rod and the first pellet have moved into the barrel of the needle and wherein the trigger is then released;

(i) a first return means which moves the drive rod back into the pistol grip means after the trigger means has been released; and (j) a second return means which moves the head means supporting the needle and the carrier means back into the nose of the gun apparatus along the longitudinal axis and along the slot in the nose of the gun apparatus after the trigger means has been released, wherein the advancing means of the carrier means registers a second pellet along the longitudinal axis in the head means after the first return means moves the drive rod out of the first opening in the head means and out of the opening in the carrier means and back into the pistol grip means and after the second return means moves the head means which supports the needle and the carrier means back into the nose of the gun apparatus.

4. A hand held gun apparatus for implanting a pellet into an animal which comprises:

(a) a hollow needle having a barrel for implanting the pellet into the animal along a longitudinal axis of the needle;

(b) a head means mounted in a nose of the gun apparatus and being linearly moveable in the gun apparatus along the longitudinal axis, the head means supporting the needle at a first end and having a second end opposite the first end traversed by a first opening along the longitudinal axis and through the head means and into the barrel of the needle, and the head means having a second opening;

(c) a carrier means detachably mounted in the second opening of the head means along a second axis, perpendicular to the longitudinal axis, wherein the carrier means is linearly moveable with the head mens along the longitudinal axis in a slot in the nose of the gun apparatus and provides for a plurality of pellets and wherein the carrier means holds a first pellet in an opening through the carrier means, and along the longitudinal axis and the first opening through the head means so that the first pellet can pass through the barrel of the needle;

(d) a pistol grip means supporting the head means;

(e) a drive rod mounted on the pistol grip means and linearly moveable along the longitudinal axis and through the first opening between the first and second ends of the head means and into the barrel of the needle;

(f) a first actuating means mounted inside of the pistol grip means for moving the drive rod;

(g) a second actuating means mounted in the pistol grip means for moving the head means;

(h) a trigger means mounted on the pistol grip means and actuatable by the fingers to move the first actuating means and the second actuating means, wherein when the trigger means is actuated, the trigger means engages a first linkage means forming the first actuating means which moves the drive rod into the first opening in the head means and into the opening through the carrier means where the drive rod engages the first pellet and moves the first pellet through the opening in the carrier means, through the first opening in the head means and into the barrel of the needle and wherein when the trigger means is actuated, the trigger means engages a second linkage means forming the second actuating means which moves the head means supporting the needle and the carrier means into the pistol grip means with the carrier means moving in the slot in the nose of the gun apparatus, after the drive rod and the first pellet have moved into the barrel of the needle, and wherein the trigger is then released;

(i) a first spring means for moving the drive rod back into the pistol grip means after the trigger means has been released; and (j) a second spring means for moving the head means, supporting the needle and the carrier means, back into the nose of the gun apparatus along the longitudinal axis and along the slot in the nose of the gun apparatus after the trigger means has been released wherein a second pellet in the carrier means is registered along the longitudinal axis in the head means after the first spring means moves the drive rod out of the first opening in the head means and out of the opening in the carrier means and back into the pistol grip means and after the second spring means moves the head means which supports the needle back into the nose of the gun apparatus.

5. The apparatus of claim 4 wherein the carrier means has opposed top and bottom ends, opposed front and rear sides and spaced apart first and second lateral sides between the top and bottom ends wherein there are spaced apart first and second openings in the first and second lateral sides along the longitudinal axis and adjacent to the top end where the carrier means is supported in the second opening in the head means, and wherein when the trigger means is actuated, the drive rod moves into the first opening in the first lateral side of the carrier means where it engages the first pellet and then moves the first pellet through the second opening in the second lateral side of the carrier means and into the barrel of the needle.

6. The apparatus of claim 5 wherein a third spring means in the carrier means urges a plate means between the first and second lateral sides of the carrier means from the bottom end to the top end so that the plate means advances pellets along the second axis for registering the second pellet along the longitudinal axis in the head means after the first spring means has moved the drive rod back into the pistol grip means and after the second spring means has moved the head means which supports the needle and the carrier means back into the nose of the gun apparatus along the longitudinal axis and along the slot in the nose of the gun apparatus, after the trigger means has been released.

7. The apparatus of claim 6 wherein the front side of the carrier means has a second slot that provides for movement of a handle means mounting the plate means in the carrier means wherein the plate means can be moved toward the bottom end thereby compressing the third spring means so that pellets can be loaded into the carrier means through either of the first and second openings in the first and second lateral sides when the carrier means is not supported in the second opening in the head means.

8. The apparatus of claim 5 wherein there are opposed grooves in the first and second lateral sides adjacent to the first and second openings and opposite the top end of the carrier means wherein the grooves receive a retaining means mounted in the head means for securing the carrier means in the second opening in the head means.

9. The apparatus of claim 8 wherein the retaining means is a fourth spring means so that the grooves in the carrier means detachably receive the fourth spring means for securing the carrier means in the second opening in the head means.

10. The apparatus of claim 7 wherein the handle means of the carrier means is a screw means that is threadably mated into a threaded aperture in the plate means.

* * * * *